United States Patent
Derwin et al.

(10) Patent No.: US 10,383,657 B2
(45) Date of Patent: *Aug. 20, 2019

(54) DEVICES AND METHODS FOR TISSUE GRAFT DELIVERY

(71) Applicant: THE CLEVELAND CLINIC FOUNDATION, Cleveland, OH (US)

(72) Inventors: Kathleen A. Derwin, Shaker Heights, OH (US); Joseph P. Iannotti, Strongsville, OH (US); Ryan A. Milks, Lakewood, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 19 days.

This patent is subject to a terminal disclaimer.

(21) Appl. No.: 14/955,103

(22) Filed: Dec. 1, 2015

(65) Prior Publication Data

US 2016/0106459 A1   Apr. 21, 2016

Related U.S. Application Data

(63) Continuation of application No. 14/212,174, filed on Mar. 14, 2014, now Pat. No. 9,265,524.

(60) Provisional application No. 61/793,900, filed on Mar. 15, 2013.

(51) Int. Cl.
*A61F 2/08* (2006.01)
*A61B 17/34* (2006.01)
*A61B 17/04* (2006.01)
*A61B 17/06* (2006.01)

(52) U.S. Cl.
CPC ...... *A61B 17/3421* (2013.01); *A61B 17/3468* (2013.01); *A61F 2/0805* (2013.01); *A61B 17/0482* (2013.01); *A61B 17/0483* (2013.01); *A61B 17/0485* (2013.01);
(Continued)

(58) Field of Classification Search
CPC .......... A61B 17/3433; A61B 5/150389; A61B 5/150396; A61B 5/150526; A61B 17/3421; A61B 17/3468; A61B 2017/3454; A61B 17/34; A61B 17/3401; A61M 2022/0656;
(Continued)

(56) References Cited

U.S. PATENT DOCUMENTS 5,255,691 A * 10/1993 Otten ................... A61N 1/0551
                                                            607/117
5,330,441 A    7/1994 Prasad
5,403,344 A    4/1995 Allen
(Continued)

OTHER PUBLICATIONS

PCT International Search Report and Written Opinion for PCT/US2014/028070, dated Jul. 1, 2014, pp. 1-13.

*Primary Examiner* — George J Ulsh
(74) *Attorney, Agent, or Firm* — Tarolli, Sundheim, Covell & Tummino LLP

(57) ABSTRACT

One aspect of the present disclosure relates to a cannula for passing a tissue graft through soft tissue. The cannula can comprise an elongated body including oppositely disposed first and second ends and an axis that extends between the first and second ends. The elongated body can further include a passage extending between the first and second ends. The second end can include a curved portion that terminates at a sharpened, pointed tip configured to pierce and/or cut soft tissue at the surgical repair site. The tip can be axially offset from the axis of the elongated body at an angle that is less than 180°.

7 Claims, 10 Drawing Sheets

(52) U.S. Cl.
CPC ............... *A61B 2017/06052* (2013.01); *A61B 2017/3433* (2013.01); *A61B 2017/3454* (2013.01)

(58) Field of Classification Search
CPC .... A61M 25/065; A61F 2/0805; A61F 2/1662
USPC ..................................................... 623/23.72
See application file for complete search history.

(56) References Cited

U.S. PATENT DOCUMENTS

| | | | |
|---|---|---|---|
| 5,462,560 | A | 10/1995 | Stevens |
| 5,669,925 | A | 9/1997 | Saunders |
| 5,895,395 | A | 4/1999 | Yeung |
| 5,897,572 | A | 4/1999 | Schulsinger |
| 5,948,002 | A | 9/1999 | Bonutti |
| 6,249,707 | B1 | 6/2001 | Kohnen et al. |
| 6,626,919 | B1* | 9/2003 | Swanstrom ........ A61B 17/0643 606/153 |
| 7,963,972 | B2 | 6/2011 | Forester et al. |
| 8,241,298 | B2 | 8/2012 | Sengun et al. |
| 2001/0041916 | A1* | 11/2001 | Bonutti ............. A61B 17/0401 606/232 |
| 2002/0022764 | A1 | 2/2002 | Smith |
| 2004/0267276 | A1 | 12/2004 | Camino et al. |
| 2005/0113736 | A1 | 5/2005 | Orr et al. |
| 2005/0182470 | A1 | 8/2005 | Cross, Jr. |
| 2007/0179455 | A1* | 8/2007 | Geliebter .............. A61M 5/329 604/272 |
| 2007/0249992 | A1 | 10/2007 | Bardy |
| 2009/0281551 | A1* | 11/2009 | Frey .................... A61B 17/025 606/99 |
| 2012/0239145 | A1 | 9/2012 | Peterson et al. |
| 2014/0257313 | A1 | 9/2014 | Frey |

* cited by examiner

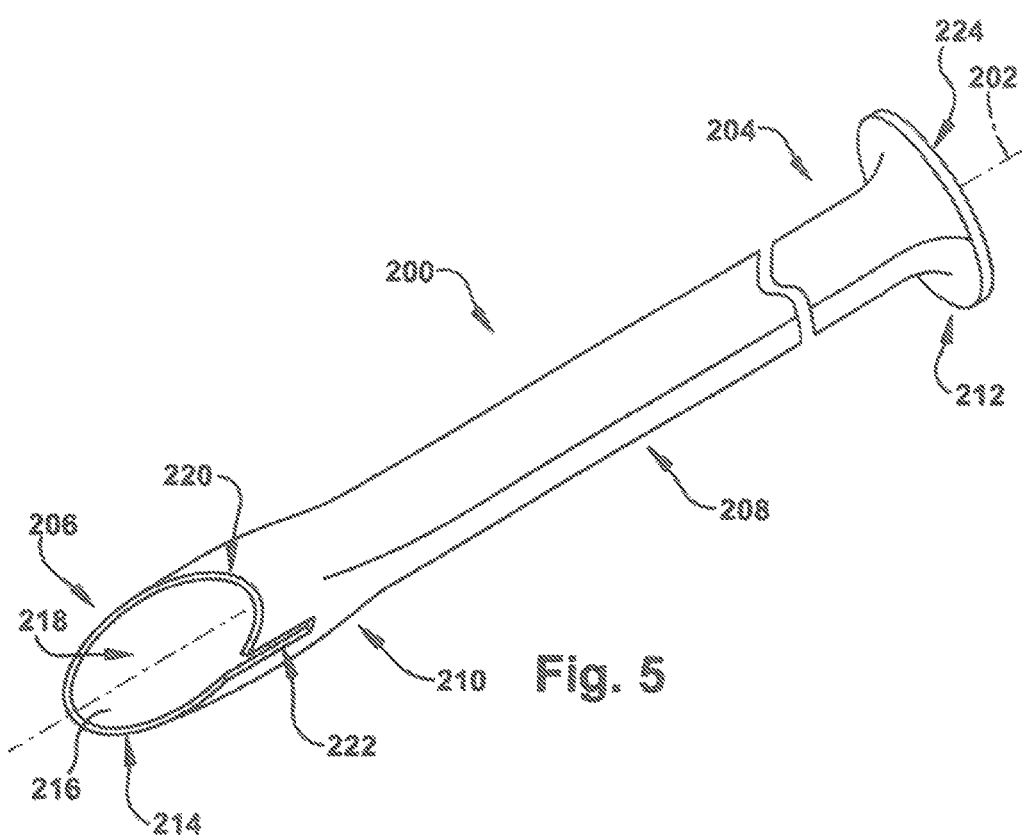

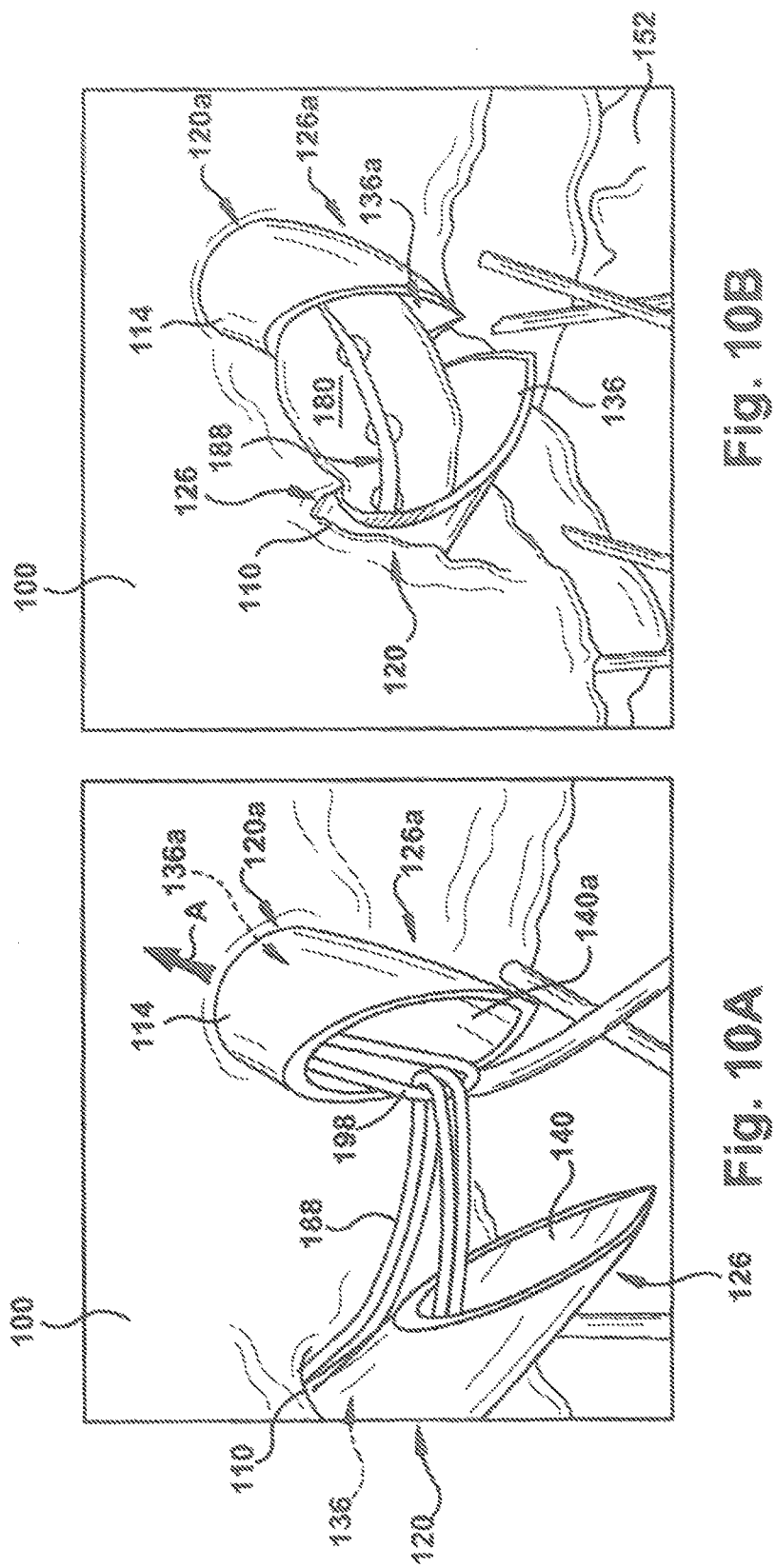

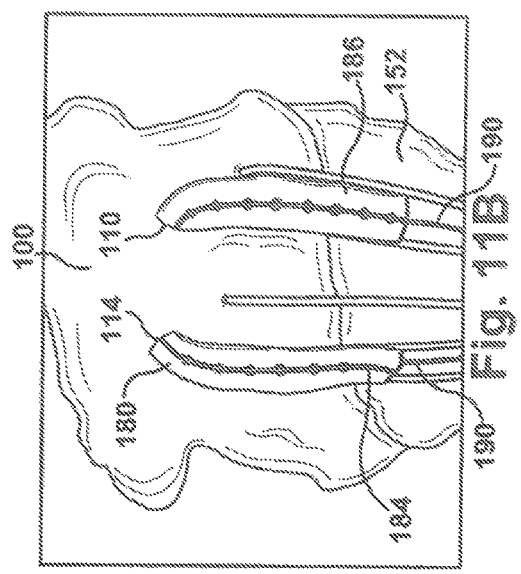
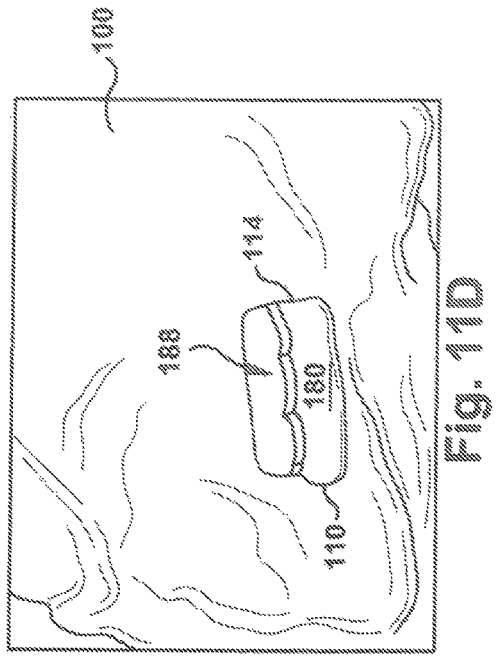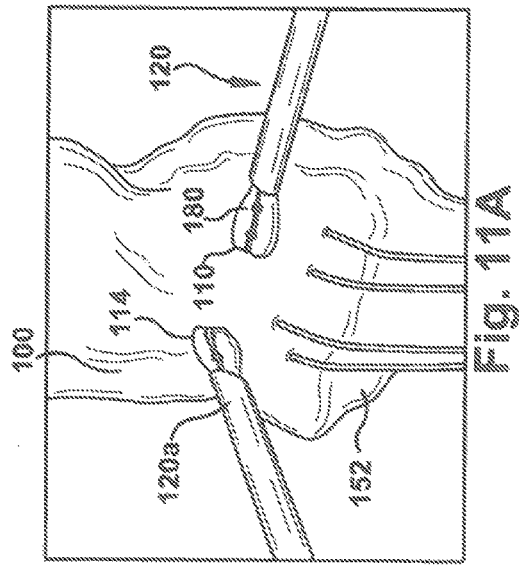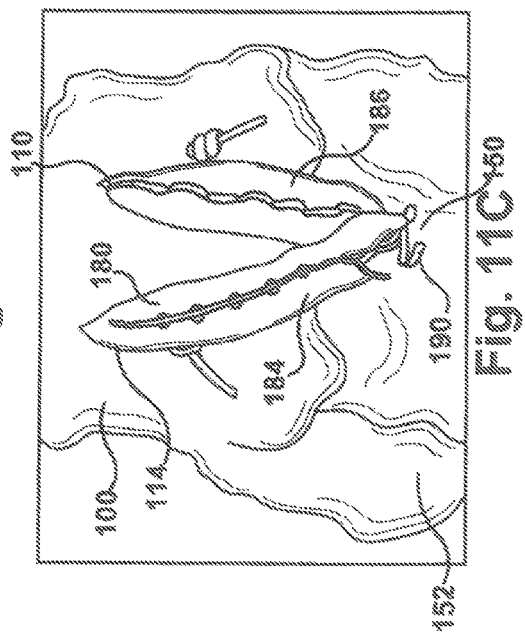

DEVICES AND METHODS FOR TISSUE GRAFT DELIVERY

RELATED APPLICATION

This application is a continuation of U.S. patent application Ser. No. 14/212,174, filed Mar. 14, 2014, which claims the benefit of U.S. Provisional Patent Application Ser. No. 61/793,900, filed Mar. 15, 2013, the entirety of each of the aforementioned applications is hereby incorporated by reference for all purposes.

TECHNICAL FIELD

The present disclosure relates generally to soft tissue repair and, in particular, to devices and methods for passing a tissue graft through a soft tissue.

BACKGROUND

Current treatment for rotator-cuff tears is to suture the torn tendon back to the bone of the humeral head. The sutures hold the tendon in contact with the bone, preferably long enough for the tendon to heal to the bone and form a bridge that will re-establish the tendon-bone connection and restore normal function. The sutures that are used possess sufficient tensile strength to retain the tendon and bone together during the healing process. However, the tendon is a fibrous tissue that can be torn by the sutures. The sutures can align with the fascicular structure of the tendon and tear through it under sufficient tensile force undoing the surgical repair before tendon-to-bone healing is complete. The sutures can also tear through the bone under sufficient force, particularly in older subjects who form the bulk of rotator-cuff-tear patients and whose bones tend to be more osteoporotic. Reinforcement of the sutures to help maintain integrity of the rotator cuff repair is therefore desirable.

SUMMARY

The present disclosure relates generally to soft tissue repair and, in particular, to devices and methods for passing a tissue graft through a soft tissue.

One aspect of the present disclosure relates to a cannula for passing a tissue graft through soft tissue. The cannula can comprise an elongated body including oppositely disposed first and second ends and an axis that extends between the first and second ends. The elongated body can further include a passage extending between the first and second ends. The second end can include a curved portion that terminates at a sharpened, pointed tip configured to pierce and/or cut soft tissue at the surgical repair site. The tip can be axially offset from the axis of the elongated body at an angle that is less than 180°

Another aspect of the present disclosure relates to a method for reinforcing soft tissue. One step of the method can include providing at least one cannula having a passage and an end. At least one opening can be formed in the soft tissue with the end of the at least one cannula. Next, a tissue graft can be passed through the passage of the at least one cannula such that the tissue graft extends through the at least one opening. The at least one cannula can then be removed from the at least one opening, and the tissue graft can be secured to the bone to reinforce the soft tissue.

Another aspect of the present disclosure can relate to a method for reinforcing soft tissue. One step of the method can include providing first and second cannulas, each of which includes a passage and a cutting end. First and second openings can be formed in the soft tissue with the cutting end of each of the first and second cannulas, respectively. Next, a tissue graft can be passed through the passage of the first cannula such that the tissue graft extends through the first opening. The tissue graft can then be accessed within the first cannula through the passage of the second cannula. The tissue graft can be drawn into the passage of the second cannula such that the tissue graft simultaneously extends through the first opening and the second opening in the soft tissue. Each cannula can be removed from each opening; whereafter the tissue graft can be secured to the bone to reinforce the soft tissue.

BRIEF DESCRIPTION OF THE DRAWINGS

The foregoing and other features and advantages of the present disclosure will become apparent to those skilled in the art to which the present disclosure relates upon reading the following description with reference to the accompanying drawings, in which:

FIG. 5 is a schematic illustration showing a cannula for deploying a tissue graft according to another aspect of the present disclosure;

FIGS. 10A-B are photographs illustrating tissue graft transfer from one cannula to the other cannula beneath the soft tissue of FIGS. 9A-D;

FIGS. 11A-D are photographs illustrating removal of the cannulas in FIGS. 10A-B from the soft tissue, followed by tissue graft securement to bone.

DETAILED DESCRIPTION

Definitions

Figure 1:
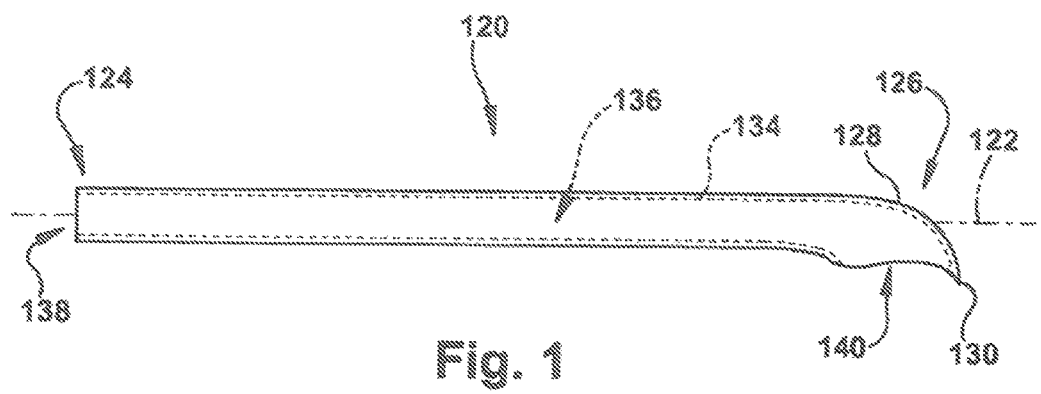
FIG. 1 is a side view of a cannula for deploying a tissue graft in accordance with one aspect of the present disclosure.

Unless defined otherwise, all technical and scientific terms used herein have the same meaning as is commonly understood by one of skill in the art to which the present disclosure pertains.

In the context of the present disclosure, the singular forms "a", "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y".

As used herein, phrases such as "from about X to Y" can mean "from about X to about Y".

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "beneath", "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

Overview

The present disclosure relates generally to surgical soft tissue repair and, in particular, to devices and methods for passing a tissue graft through a soft tissue. The use of tissue grafts for soft tissue repair procedures typically requires the use of multiple instruments at different times during a given repair procedure. This not only increases the time and costs associated with such procedures, but also the risk of tearing and/or contaminating the tissue graft(s). Advantageously, the present disclosure provides devices and methods for delivering a tissue graft to a surgical repair site using a cannula (or cannulas) that can simultaneously accesses the surgical repair site, form the tissue openings, and deploy the tissue graft. An additional advantage is that a tissue graft can be passed through soft tissue using arthroscopic techniques and does not require open surgery. As discussed below, the devices and methods of the present disclosure may be used in a variety of human and veterinary surgical applications including, but not limited to, the repair of a tendon or ligament to bone, (e.g., rotator cuff tendon repair) the repair of a tendon or ligament mid-substance, the repair of fascia or muscle including the ventral abdominal wall, the repair of skin, repair of pelvic organs or tissues, repair of vascular organs or tissues or the repair of any solid, soft connective tissue. In one instance, the surgical repair site can include soft tissue that is undergoing or has undergone surgical repair. In instances where the soft tissue has undergone surgical repair, it may also be referenced herein as "surgically-repaired soft tissue". Alternatively, the surgical repair site can include soft tissue that is damaged but has not been surgically repaired.

Devices

Figure 2:
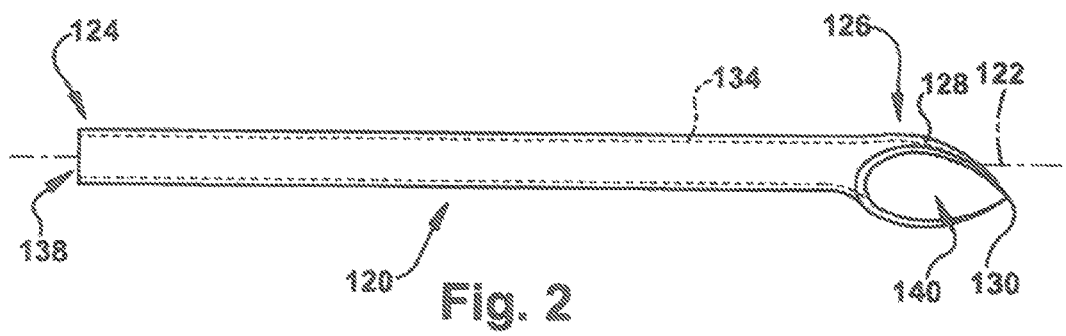
FIG. 2 is a top view of the cannula in FIG. 1.

One aspect of the present disclosure can include a cannula 120 (FIGS. 1-2) for passing a tissue graft through a soft tissue. The cannula 120 has a generally elongated body with an oppositely disposed first and second ends 124 and 126 and an axis 122 that extends from the first end 124 to the second end 126. The elongated body of the cannula 120 further includes an inner surface 134 that defines a passage 136, which extends through the entire length of the cannula 120. The passage 136 terminates at an opening 138 at the first end 124 of the cannula 120, and at an opening 140 at the second end 126 of the cannula 120.

Figure 3:
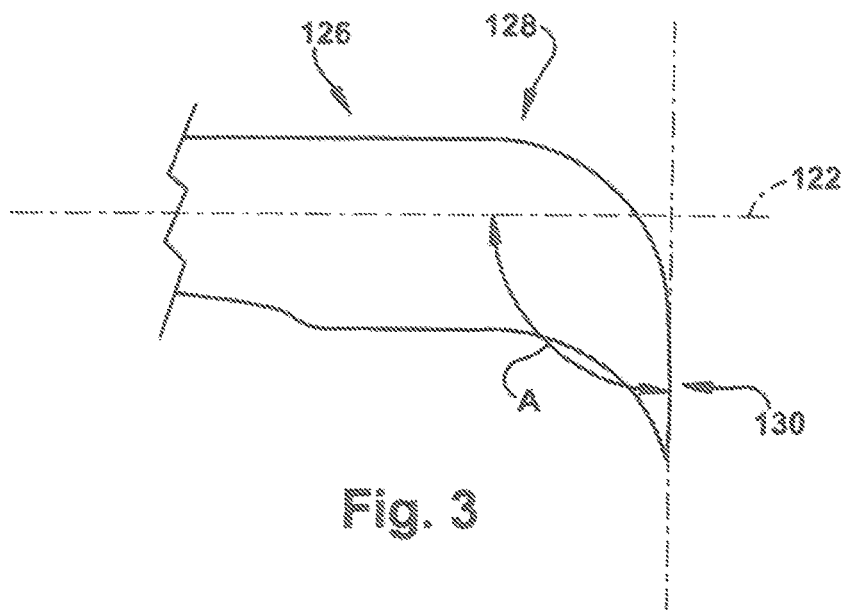
FIG. 3 is a magnified view showing a second end of the cannula in FIG. 1.

The second end 126 includes a curved portion 128 that terminates at a sharp or pointed tip 130 configured to puncture, pierce or cut solid, soft tissue, e.g., a tendon. The second end 126 therefore functions as a cutting end of the cannula 120. The curved portion 128 extends at a desired angle relative to the axis 122 that takes into consideration particular anatomical geometry and the ability of the tip to pierce and/or cut soft tissue at a surgical site. As shown in FIG. 3, the tip 130 can be axially offset from the axis 122 of the elongated body of the cannula 120 at an angle, A, that is less than 180°. An angle A of less than 180° (e.g., about 30°) advantageously provides the tip 130 with the ability to effectively puncture, pierce or cut solid, soft tissue (e.g., a tendon).

The cross-sectional shape of all or only a portion of the cannula 120 is substantially circular; although, other shapes, such as elliptical, oblong, rectangular, square, triangular, or any other polygonal shape or combination thereof are contemplated. The cannula 120 can have a diameter of about 2.5 mm to about 10 mm, although smaller or larger sizes are contemplated. In one example, the cannula can have a diameter of about 5 mm. The cannula 120 can be used as a stand-alone working cannula or be sized to pass within a standard arthroscopic working cannula (not shown). The cannula 120 can be made of, or formed, from one or more biocompatible materials, such as stainless steel, titanium, or a biocompatible plastic. All or only a portion of the cannula 120 may be transparent to allow a user to visualize a tissue graft within the passage 136.

Figure 4:
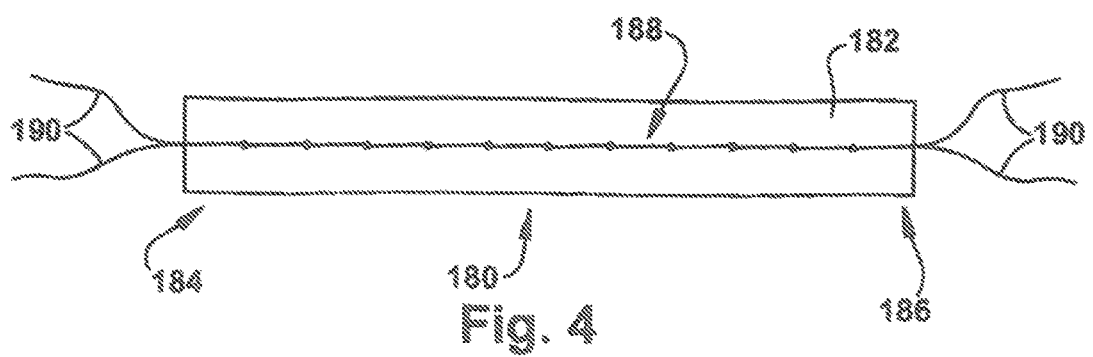
FIG. 4 is a schematic illustration of a tissue graft for use with the cannula in FIG. 1.

An example of a tissue graft 180 to be deployed to the surgical repair site by the cannula 120 is illustrated in FIG. 4. The tissue graft 180 is shown having a substantially rectangular configuration; however, it will be appreciated that the tissue graft may have any configuration known to those having ordinary skill. For example, the tissue graft 180 can include a trans-tendon repair device with suture tails, as described in U.S. Patent Publication No. 2012/0239145A1. Other examples of tissue grafts that may be delivered to a surgical site according to the present disclosure are described in U.S. Patent Publication Nos. 2011/0014153A1, 2013/0053961A1 and 2013/0116799A1.

As shown in FIG. 4, the tissue graft 180 extends from a first end 184 to a second end 186. The tissue graft 180 includes tissue 182 and attachment means 188 that are associated with, connected to, and/or integrated into the tissue 182. In some instances, the attachment means 188 can be a suture (e.g., a temporary delivery suture) or other suitable means for securing a tissue graft to bone. In other instances, the attachment means can comprise a reinforcement means as disclosed, for example, in U.S. Patents Nos. 2011/0014153A1, 2013/0053961A1, and 2013/0116799A1. The tissue 182 may be formed from a biocompatible material, such as a synthetic material, extracellular matrix (ECM) material, biologic material, or any combination thereof. The cross-section of the tissue graft 180 is substantially rectangular or square, although other shapes are contemplated. In one instance, the tissue graft 180 and the passage 136 of the cannula 120 can have an identical or similar shape (cross-sectional shape) as one another. The attachment means 188 constitutes a plurality of stitches integrated into the tissue 182 in a predetermined configuration or pattern. One or more free ends 190 of the attachment means 188 extend beyond the periphery of the tissue 182. In one instance, a pair of free ends 190 extend beyond the tissue periphery at each end 184, 186 of the tissue graft 180.

Figure 6A:
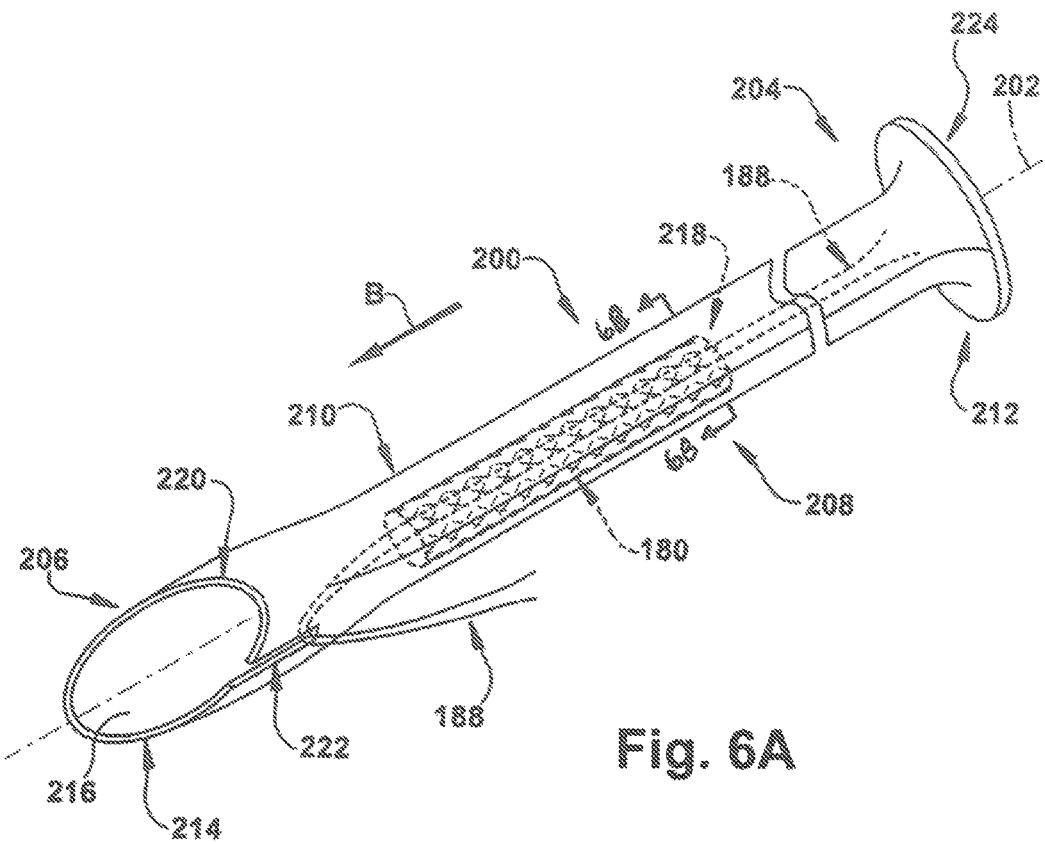
FIG. 6A is a schematic illustration showing a tissue graft being deployed through the cannula in FIG. 5.
Figure 6B:
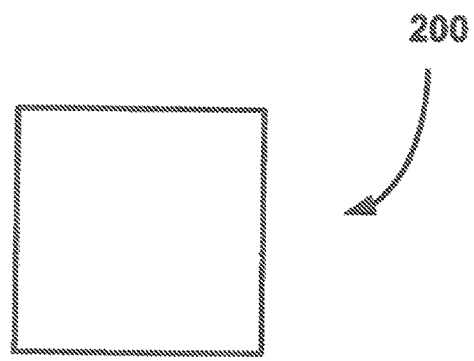
FIG. 6B is a cross-sectional view taken along line 6B-6B in FIG. 6A.

FIGS. 5-6B illustrate a cannula 200 for delivering a tissue graft to a surgical repair site according to another aspect of the present disclosure. Except as described below, the cannula 200 can be identically constructed as the cannula 120 shown in FIG. 1-2 and described above.

The cannula 200 has a generally elongated shape and extends along an axis 202 from a first end 204 to a second end 206. A passage 218 extends between the first and second ends 204 and 206. A bell-shaped receptacle 212 extends radially outward from the first end 204. The receptacle 212 is configured to facilitate entry of a tissue graft into the passage 218. The second end 206 includes a portion 214 configured to puncture, pierce or cut solid, soft tissue. The second end 206 therefore functions as a cutting end of the cannula 200. Although the second end 206 is illustrated as being substantially centered about the axis 202, it will be appreciated that the second end may be curved relative to the axis (not shown) similar to the curved portion 128 of the cannula 120. For example, the second end 206 may terminate at a sharp or pointed tip (not shown) and be axially offset from the axis 202 at an angle less than 180° (e.g., about 30°).

An inner surface 216 of the cannula 200 defines the passage 218, which extends through the entire length of the cannula 200. The passage 218 terminates at an opening 224 at the first end 204 of the cannula 200, and at an opening 220 at the second end 206 of the cannula 200. The cross-sectional shape of the cannula 200 can be uniform along the entire length of the cannula 200 or alternatively, may vary in one or more locations along the length of the cannula 200. The first end 204 of the cannula 200 can have any cross-sectional shape, such as, circular or oblong. In some instances, the first end 204 can have a cross-section that is different than a cross-section of the elongated body. In some instances, the elongated body can have a non-circular cross-section. In one example, the first end 204 can have a circular or oblong cross-section, the elongated body can have a rectangular cross-section, and the second end 206 can have a circular cross-section. This configuration advantageously facilitates easy entry of the tissue graft 180 at the first end 204 while the rectangular cross-section flattens the tissue graft 180 to keep it from twisting as it is delivered through the passage 218. In some instances, the rectangular portion 208 can extend from the receptacle 212 to a point adjacent the second end 206 of the cannula 200. The rectangular portion 208 can terminate at a portion 210, which has a circular cross-section.

The cannula 200 can be made of, or formed from, one or more biocompatible materials, such as stainless steel, titanium, or a biocompatible plastic. All or only a portion of the cannula 200 may be transparent to allow a user to visualize the tissue graft within the passage 218.

In some instances, a slot 222 can extend along the length of the cannula 200 from the opening 220 towards the first end 204 of the cannula. In one example, the slot 222 can extend from the opening 220 towards the first end 204, but terminate proximal to, at, or distal from the portion 210. The slot 222 has a width configured to receive one or more free ends 190 of the attachment means 188 in the tissue graft 180 so that damage to the attachment means 188 is advantageously mitigated or prevented during delivery of the tissue graft. If the attachment means 188 is/are wrapped around the cutting surface or cutting end, for example, damage to the attachment means would advantageously be avoided during cutting or formation of the tissue openings.

Methods

Figure 7:
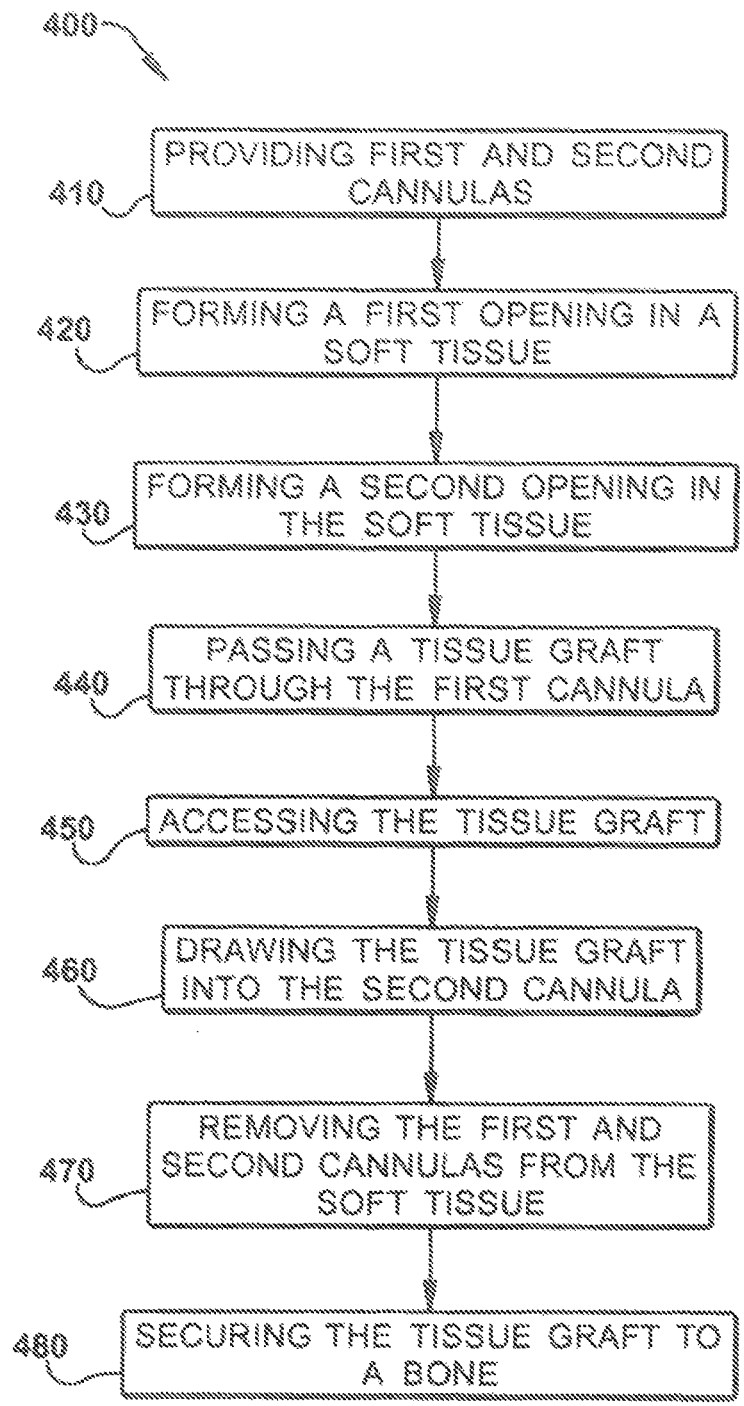
FIG. 7 is a process flow diagram illustrating a method for reinforcing soft tissue according to another aspect of the present disclosure.

Another aspect of the present disclosure can include a method 400 (FIG. 7) for reinforcing soft tissue, such as soft tissue that has previously undergone surgical repair. The method 400, at 410, can include providing first and second cannulas 120, 120a (FIGS. 8A-9D), each of which includes a passage 136 and a cutting end 130. One or both of the cannulas 120, 120a can be identically constructed as the cannula 120 shown in FIGS. 1-2 and described above. For clarity, the second cannula 120a includes the suffix "a".

Figure 8A:
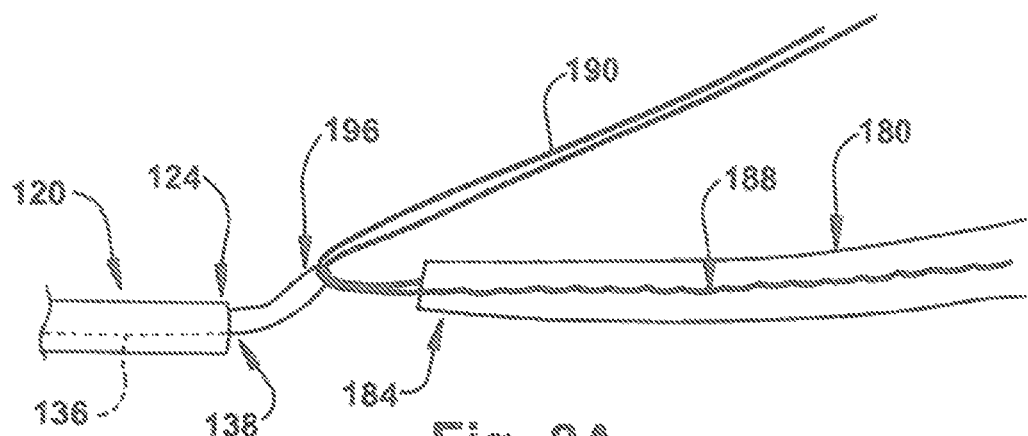
FIGS. 8A-C are photographs illustrating tissue graft loading into the cannula of FIG. 1.
Figure 8B:
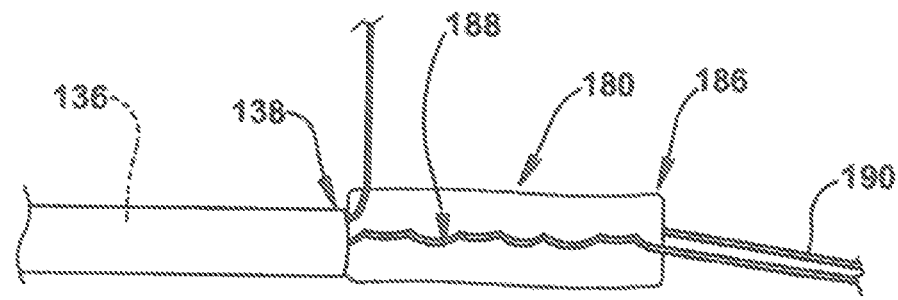
Figure 8C:
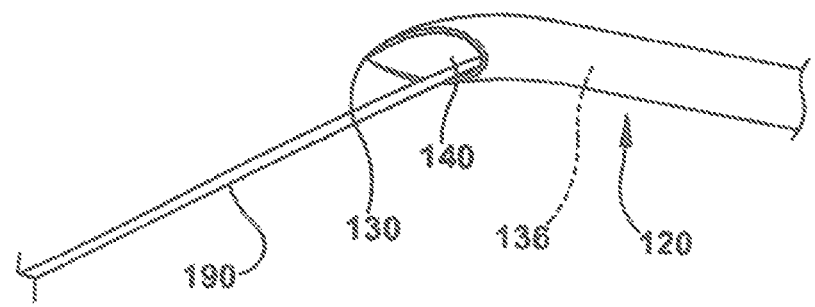

Referring to FIGS. 8A-C, the tissue graft 180 is first inserted into the passage 136 of the first cannula 120. It will be appreciated, however, that the tissue graft 180 may alternatively be inserted into the passage 136a of the second cannula 120a. The first end 184 of the tissue graft 180 is fed into the opening 138 of the first cannula 120 by pulling the free ends 190 of the attachment means 188 at the first end through the passage 136 of the first cannula with a conventional suture lasso 196 (FIG. 8A). To this end, the suture lasso 196 is fed into the opening 140 in the first cannula 120 and through the entire passage 136 until passing through the opening 138 into proximity with the free ends 190. The suture lasso 196 then captures the free ends 190 and is pulled towards the second end 126 of the first cannula 120 to pull the tissue graft 180 into the passage 136 (FIG. 8B). The free ends 190 are ultimately made to extend through the opening 140 in the first cannula 120 (FIG. 8C). Configuring the tissue graft 180 and the passage 136 of the first cannula 120 with similar shapes (cross-sectional shapes) advantageously facilitates passage of the tissue graft 180 through the first cannula 120 and maintains the orientation of the tissue graft 180 relative to the first cannula 120. The tissue graft 180 is now ready for deployment into the soft tissue 100 (FIGS. 9A-D).

Figure 9A:
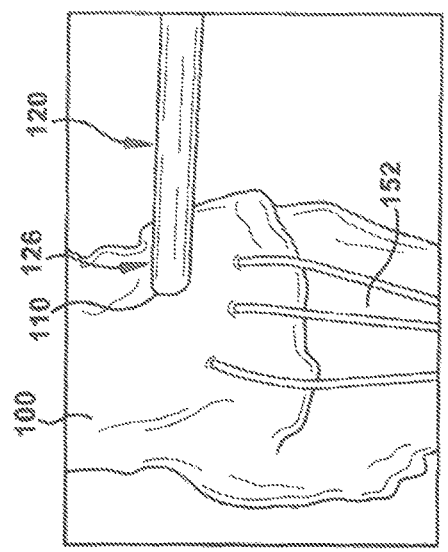
FIGS. 9A-D are photographs illustrating soft tissue penetration with two of the cannulas shown in FIG. 1.
Figure 9B:
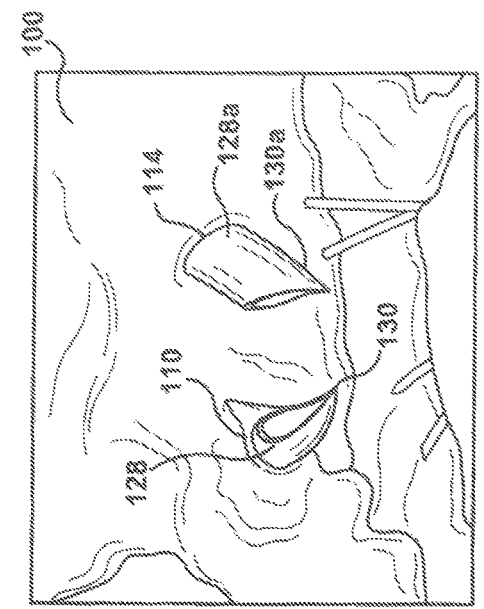
Figure 9C:
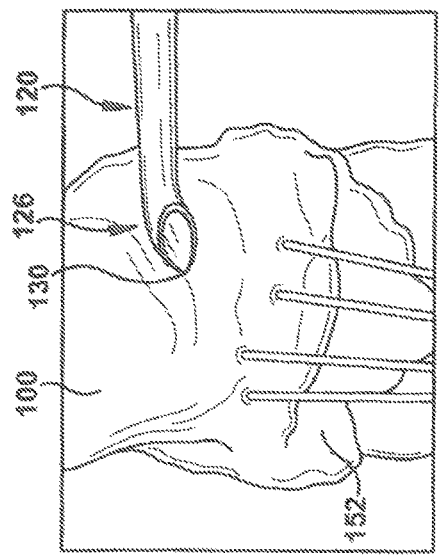
Figure 9D:
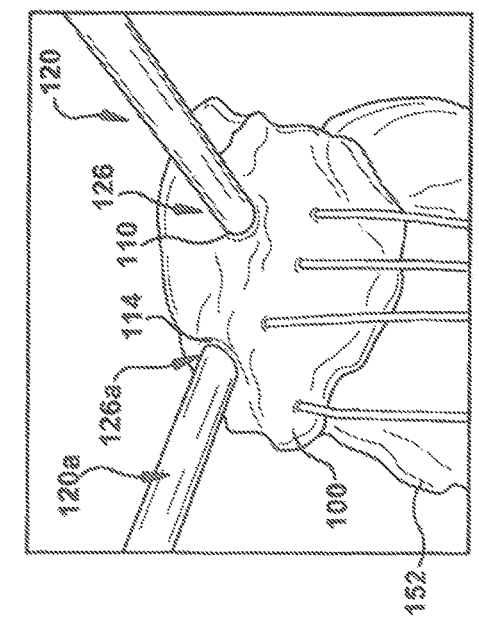

Referring to FIGS. 9A-B, the method 400 can include forming a first opening 110 in the soft tissue 100 with the cutting 126 end of the first cannula 120 (at 420). More specifically, the tip 130 of the first cannula 120 cuts, punctures, or penetrates the soft tissue 100 in an antegrade (e.g., superficial to deep) direction to form the first opening 110. The first cannula 120 is pushed through the first opening 110 until the second end 126 of the first cannula is positioned beneath the soft tissue 100 (e.g., adjacent the underlying humerus bone 150). Although not shown, the free ends 190 of the attachment means 188 at the first end 184 of the tissue graft 180 are located within or extend through the opening 140 in the first cannula 120 due to preloading the tissue graft within the first cannula prior to forming the first opening 110.

Referring to FIG. 9-D, the method 400 can also include forming a second opening 114 in the soft tissue 100 with the cutting 126a end of the second cannula 120a (at 430). More specifically, the tip 130a of the second cannula 120a punctures or penetrates the soft tissue 100 in an antegrade direction to form a second opening 114 that is spaced apart from, but in proximity to, the first opening 110. The second cannula 120a is pushed through the second opening 114 until the second end 126a of the second cannula is positioned beneath the soft tissue 100 adjacent the underlying bone. The curved portions 128, 128a are oriented to extend towards one another (e.g., face one another) beneath the soft tissue 100.

At 440, the method 400, can include passing the tissue graft 180 through the passage 136 of the first cannula 120 such that the tissue graft 180, while still being partially housed in the first cannula 120, extends through the first opening 110 in the soft tissue 100.

The method 400 further includes the step of accessing the tissue graft 180 within the first cannula 120 through the passage of the second cannula 136a (at 450). Referring to FIG. 10A, for example, a standard suture grasper 198 can be inserted into the passage 136a of the second cannula 120a via the opening 138a. The grasper 198 can then be extended through the opening 140a to a position near the free ends 190 of the attachment means 188 (e.g., adjacent to the opening 140) in the first cannula 120. The suture grasper 198 is then actuated or operated to grasp the free ends 190 as shown in FIG. 10B.

At 460, the method 400 can further include drawing the tissue graft 180 into the passage of the second cannula 120a such that the tissue graft simultaneously extends through the first opening and second openings 110 and 114.

Following 460, the suture grasper 198 is pulled or retracted in the direction indicated generally by arrow A (FIG. 10A) towards the first end 124a of the second cannula 120a, which pulls the free ends 190 of the attachment means 188 in the direction A. Additional pulling of the suture grasper 198 in the direction A results in the first end 184 of the tissue graft 180 being pulled into the passage 136a of the second cannula 120a (FIG. 10B). Consequently, this places the tissue graft 180 in a position whereby the tissue graft 180 simultaneously extends in a mattress configuration through both the first opening 110 and the second opening 114 in the soft tissue 100.

Referring to FIGS. 11A-B, both of the cannulas 120, 120a can be removed from the respective openings 110, 114 (at 470), thereby leaving the tissue graft 180 in place and spanning the soft tissue openings 110, 114 beneath the tissue. At 480, the method 400 can also include securing the tissue graft 180 to the bone to reinforce the soft tissue 100. For example, as shown in FIG. 11C, the free ends 190 of the attachment means 188 can be attached to a bone anchor 150 on the proximal humerus 152 using standard surgical tools and techniques. The tissue graft 180, once secured to the humerus 152 and extending through the openings 110, 114 in the soft tissue 100, can advantageously reinforce the soft tissue 100 at the surgical repair site. It will be appreciated that, in some instances, the delivered tissue graft 180 can serve as the soft tissue repair itself (e.g., instead of reinforcing the soft tissue).

The methodology of the present disclosure is advantageous in that the cannulas 120, 120a can perform multiple operations; namely, forming the openings 110, 114 in the soft tissue 100 and remaining in the openings while the tissue graft 180 is deployed through and between the cannulas to place the tissue graft through the soft tissue openings. More specifically, the cannulas 120, 120a advantageously both form the openings 110, 114 in the solid, soft tissue 100 and deploy the tissue graft 180 through the soft tissue to reinforce the repair in accordance with the present disclosure. The cannulas 120, 120a can also advantageously protect the tissue graft 180 during deployment into the soft tissue 100 by, for example, mitigating tearing, tangling, and/or damage of the tissue graft 180.

Although not shown, an alternative method for reinforcing soft tissue (e.g., surgically-repaired soft tissue) is described below. The method can be performed in a manner similar or identical to the method 400 described above; however, one or both of the cannulas 120, 120a can be replaced with the cannula 200 shown in FIGS. 5-6B.

In use, a tissue graft 180 can be inserted into the cannula 200 prior to introducing the cannula 200 into the soft tissue 100. The free ends 190 at the first end 184 of the tissue graft 180 can be fed into the opening 224 in the first end 204 of the cannula 200. The bell-shaped receptacle 212 at the first end 204 of the cannula 200 advantageously facilitates entry of the tissue graft 180 into the passage 218. The free ends 190 are pulled in the direction indicated by the arrow B to draw the tissue graft 180 towards the second end 206 of the cannula 200. Configuring the tissue graft 180 and the passage 218 of the cannula 200 with similar shapes (e.g., rectangular cross-sections) facilitates passage of the tissue graft 180 through the cannula 200 and advantageously helps to prevent twisting and/or kinking of the tissue graft 180 therein. In some instances, the user can visualize the tissue graft 180 moving through the passage 218 due to the transparent construction of the cannula 200. This construction allows the user to ensure that the tissue graft 180 has not twisted or kinked during delivery through the cannula 200.

The free ends 190 are passed through the slot 222 at the second end 206 to help mitigate or prevent damage to the attachment means 188 during penetration of the cannula 200 into the soft tissue 100. In some instances, a recess (not shown) may be formed in the wall of the cannula 200 that extends from the end of the slot 222 along the length of the cannula to the first end 204. In such instances, the recess receives the free ends 190 to house the free ends during introduction of the cannula 200 into the soft tissue 100. The remainder of the method for implanting the tissue graft 180 through the openings 110, 114 in the soft tissue 100 and securing the free ends 190 to the humerus 152 is the same as previously described for the method 400 above.

Figure 12:
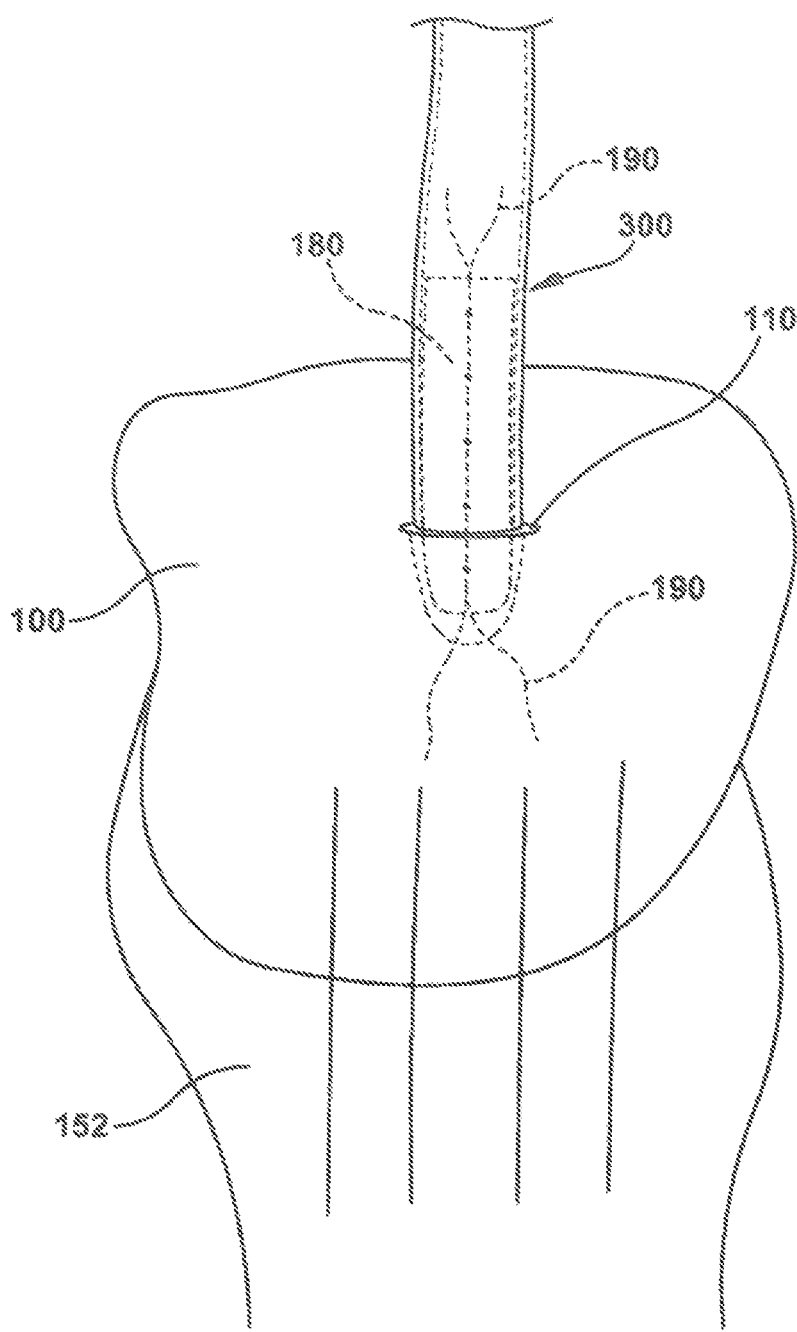
FIG. 12 is a schematic illustration showing an alternative method for deploying a tissue graft into soft tissue according to another aspect of the present disclosure.

The present disclosure is described as using a pair of cannulas to form a pair of openings in a soft tissue. It will be understood, however, that a single cannula 300 (FIG. 12) could be used to form a single opening 110 in the solid, soft tissue 100. The single cannula 300 would then deploy the tissue graft 180 into the soft tissue 100 before being removed from the single opening. Consequently, this places the tissue graft 180 in a position whereby the tissue graft 180 extends both above and beneath the soft tissue 100 through the single opening 110 in the soft tissue 100.

The free ends 190 of the attachment means 188 can then be attached to a bone anchor on the proximal humerus 152 using standard surgical tools and techniques. The tissue graft 180, once secured to the humerus 152 and extending through the opening 110 the soft tissue 100, can advantageously be used to directly repair the soft tissue 100 to the bone. Furthermore, one or more of the cannulas 120, 120a, 200, 300 could be used to form more than two openings in the soft tissue for deploying one or more tissue grafts into the soft tissue in accordance with the present disclosure. For example, one or more cannulas 120, 120a, 200, 300 could form three openings, four openings, etc., in the soft tissue 100. In each case, however, the cannula that deploys the tissue graft(s) is also the cannula that forms, e.g., cuts, pierces or punctures, the soft tissue opening through which the tissue graft(s) is/are deployed. Each tissue graft 180, once secured to the humerus 152 and extending through the opening 110 the soft tissue 100, can advantageously be used to directly repair the soft tissue 100 to the bone at its location.

The preferred embodiments of the present disclosure have been illustrated and described in detail. However, the present disclosure is not to be considered limited to the precise construction disclosed. Various adaptations, modifications, and uses of the present disclosure may occur to those skilled in the art to which the present disclosure relates, and the intention is to cover hereby all such adaptations, modifications, and uses which fall within the spirit or scope of the appended claims. For instance, although the tissue graft 180 is illustrated as including permanent attachment means that aid in deploying the tissue graft 180 into soft tissue 100, it will be understood that the attachment means 188 may be omitted and temporary delivery sutures provided in the tissue 182 to pass the tissue graft 180 through the cannulas 120, 120a, 200, 300 and into position. In such a case, the delivery sutures are then removed and the tissue 182 secured to the bone anchor 152 via suturing, etc.

All patents, publications, and references cited in the foregoing specification are hereby incorporated by reference in their entirety.

The following is claimed:

1. A cannula for passing a tissue graft through soft tissue, the cannula comprising:
    an elongated body including oppositely disposed first and second ends and an axis that extends between the first and second ends, the elongated body further including a passage extending between the first and second ends, a terminal end of the first end of the elongated body having a bell-shaped configuration with an opening extending therethrough, whereby the bell-shaped configuration is shaped and dimensioned to facilitate entry of the tissue graft into the cannula at the terminal end of the first end via the opening and into the passage, the elongated body being substantially rigid for the purpose of being passed through soft tissue;
    wherein the cannula further comprises including a slot that extends along a length of the elongated body from an opening at the second end towards the first end;
    wherein the second end includes a non-linear curved portion that terminates at a sharpened, pointed tip configured to pierce and/or cut soft tissue at the surgical repair site;
    wherein the tip is axially offset from the axis of the elongated body at an angle that is less than 180°.

2. The cannula of claim 1, wherein all or only a portion of the elongated body is transparent.

3. The cannula of claim 1, wherein the slot has a width configured to receive one or more free ends of an attachment means associated with the tissue graft so that damage to the attachment means is mitigated or prevented during formation of an opening in the soft tissue.

4. The cannula of claim 1, wherein the elongated body has a non-circular cross-section.

5. The cannula of claim 1, wherein the axis is a central longitudinal axis of the elongated body, the non-linear curved portion intersecting the axis.

6. A cannula for passing a tissue graft through soft tissue, the cannula comprising:
    an elongated body including oppositely disposed first and second ends and an axis that extends between the first and second ends, the elongated body further including a passage extending between the first and second ends, a terminal end of the first end of the elongated body having a bell-shaped configuration with an opening extending therethrough, whereby the bell-shaped configuration is shaped and dimensioned to facilitate entry of the tissue graft into the cannula at the terminal end of the first end via the opening and into the passage, the elongated body being substantially rigid for the purpose of being passed through soft tissue;
    wherein the second end includes a non-linear curved portion that terminates at a sharpened, pointed tip configured to pierce and/or cut soft tissue at the surgical repair site;
    wherein the first end has a cross-section that is different than a cross-section of the elongated body and a cross-section of the second end;
    wherein the cross-section of the first end of the elongated body has oblong cross-section, the cross-section of the elongated body has a rectangular cross-section, and the cross-section of the second end has a circular cross-section.

7. A tissue graft delivery system comprising:
    a cannula, comprising:
        an elongated body including oppositely disposed first and second ends and an axis that extends between the first and second ends, the elongated body further including a passage extending between the first and second ends, a terminal end of the first end of the elongated body having a bell-shaped configuration with an opening extending therethrough, whereby the bell-shaped configuration is shaped and dimensioned to facilitate entry of a tissue graft into the cannula at the terminal end of the first end via the opening and into the passage;
        a curved portion at the second end that terminates at a sharpened, pointed tip configured to pierce and/or cut soft tissue at the surgical repair site, the tip being axially offset from the axis of the elongated body at an angle that is less than 180°; and
        a slot that extends along a length of the elongated body from an opening at the second end toward the first end; and
    wherein the tissue graft entering into the cannula at the terminal end of the first end via the opening and into the passage comprises:
        tissue; and
        attachment means associated with the tissue, the attachment means having one or more free ends that are receivable in the slot such that damage to the attachment means is mitigated or prevented during formation of an opening at a surgical repair site.

* * * * *